United States Patent [19]
Lee et al.

[11] Patent Number: 6,162,888
[45] Date of Patent: Dec. 19, 2000

[54] METHOD OF MAKING SILICONE POLYETHER COPOLYMERS HAVING REDUCED ODOR

[75] Inventors: Kenneth Michael Lee; Lenin James Petroff, both of Bay City; William James Schulz, Jr., Midland, all of Mich.

[73] Assignee: Dow Corning Corporation, Midland, Mich.

[21] Appl. No.: 09/312,795

[22] Filed: May 17, 1999

[51] Int. Cl.[7] .............................. C08G 77/04; C08F 7/08
[52] U.S. Cl. ................................ 528/25; 528/14; 528/15; 528/31; 528/33; 556/445; 525/338; 525/339; 525/474; 525/479
[58] Field of Search ......................... 528/14, 15, 25, 528/31, 33; 525/338, 339, 474, 479; 556/445

[56] References Cited

U.S. PATENT DOCUMENTS

| | | | |
|---|---|---|---|
| 2,823,218 | 2/1958 | Speier et al. | 260/448.2 |
| 3,419,593 | 12/1968 | Willing | 260/448.2 |
| 4,515,979 | 5/1985 | Otsuki et al. | 556/445 |
| 4,847,398 | 7/1989 | Mehta et al. | 556/445 |
| 5,118,764 | 6/1992 | Ichinobe et al. | 525/398 |
| 5,225,509 | 7/1993 | Heinrich et al. | 528/12 |
| 5,288,831 | 2/1994 | Ichinobe et al. | 528/25 |
| 5,696,192 | 12/1997 | Harashima | 524/366 |
| 5,869,727 | 2/1999 | Crane et al. | 556/445 |

FOREIGN PATENT DOCUMENTS

| | | |
|---|---|---|
| 7-330907 | 12/1995 | Japan . |
| 91-65315 | 6/1997 | Japan . |
| 91-65318 | 6/1997 | Japan . |
| 11335463 | 12/1999 | Japan . |

OTHER PUBLICATIONS

Derwent Abstract of JP 1135463 Dec. 1999 to Nippon Unicar.

*Primary Examiner*—Robert Dawson
*Assistant Examiner*—Jeffrey B. Robertson
*Attorney, Agent, or Firm*—Timothy J. Troy

[57] ABSTRACT

The present invention relates to a method of making a silicone polyether comprising (I) reacting a mixture comprising an olefin functional polyether, an organohydrogensiloxane, and a homogeneous transition metal hydrosilylation catalyst, and (II) subjecting the product of (I) to hydrogen gas. The method of this invention reduces the amount of olefinic species present which are precursors to odorous compounds. Thus the method of this invention reduces the amount of odor in the silicone polyether product. These odors are objectionable, particularly in personal care applications.

27 Claims, No Drawings

METHOD OF MAKING SILICONE POLYETHER COPOLYMERS HAVING REDUCED ODOR

FIELD OF THE INVENTION

The present invention relates to a method of making a silicone polyether copolymer having reduced odor. More particularly this invention relates to a method of making a silicone polyether copolymer having reduced odor comprising (I) reacting a mixture comprising an alkenyl functional polyether, a polydiorganosiloxane-polyorganohydrogensiloxane copolymer, and a homogeneous transition metal hydrosilylation catalyst, and (II) subjecting the product of (I) to hydrogen gas.

BACKGROUND OF THE INVENTION

Silicone polyethers are generally prepared by reacting an alkenyl functional polyether such as an allyl polyether with a polyorganohydrogensiloxane in the presence of a platinum catalyst. In the preparation of these silicone polyethers, an excess of, for example, allyl polyether is used, and, in doing so under the conditions of the addition reaction, a portion of the allyl polyether is rearranged into propenyl polyether which is orders of magnitude slower at undergoing the addition reaction. The reaction product thus contains the silicone polyether copolymer as well as moieties of unreacted allyl polyether and unreacted propenyl polyether. These silicone polyethers are often used as active ingredients in cosmetic products. However, in some formulations they contribute a strongly noticeable, distinct and unpleasant, acrid odor which has a tendency to become stronger upon storage. The odor is generally understood to arise as a consequence of the oxidation and/or hydrolysis of the unreacted propenyl ether into propionaldehyde. This odor is an obstacle to the use of these silicone polyethers as active ingredients in many cosmetic preparations.

Attempts have been made in the past to prevent the formation of or remove the odor forming components and have involved a combination of the addition of a heterogeneous hydrogenation catalyst, hydrogenation (i.e. exposure to hydrogen gas), and some form of an acid-catalyzed hydrolysis followed by vacuum stripping. For example Japanese Patent Application No. 07330907 discloses the manufacture of a purified polyether-modified polysiloxane composition synthesized by the hydrosilylation reaction of a polyoxyalkylene with a C═C in the terminal position and a polyhydrogensiloxane. The polyether-modified polysiloxane composition is then hydrogenated in the presence of an added heterogeneous hydrogenation catalyst to saturate any residual double bonds. This has the effect of preventing the unwanted degradation of the propenyl ether; thereby preventing the formation of the odorous propionaldehyde. Other volatile components are preferably distilled off from the reaction mixture before or after hydrogenation.

Japanese Patent Application No. 9165315 discloses a skin cosmetic material which contains 0.01 to 100 wt % of a purified polyether-modified polysiloxane composition prepared by the hydrosilylation reaction of a polyoxyalkylene with a carbon-carbon double bond in the terminal position and a polyhydrogensiloxane. The material is then purified by hydrogenation in the presence of an added heterogeneous hydrogenation catalyst.

Japanese Patent Application No. 9165318 discloses a hair cosmetic containing 0.01 to 100 wt % of a purified polyether-modified polysiloxane composition prepared by the hydrosilylation reaction of a polyoxyalkylene containing a C—C double bond at the terminus with a polyhydrogensiloxane, followed by hydrogenation in the presence of an added heterogeneous hydrogenation catalyst.

Heinrich et al. in U.S. Pat. No. 5,225,509 discloses a method for deodorizing polyoxyalkylene polysiloxane mixed block copolymers wherein the polysiloxane blocks are linked to the polyether blocks through SiC linkages. Heinrich et al further discloses that hydrogen is allowed to act on the mixed block polymers in the presence of heterogeneous hydrogenation catalysts at temperatures of 20 to 200° C. and a pressure of 1 to 100 bar for a period of 0.5 to 10 hours. Heinrich et al. only discloses the use of heterogeneous hydrogenation metal catalysts or supported metals. Nowhere in Heinrich et al. are homogeneous transition metal hydrosilylation catalysts and in particular homogeneous platinum hydrosilylation catalysts disclosed or suggested as hydrogenation catalysts.

SUMMARY OF THE INVENTION

This invention relates to a method of making a silicone polyether copolymer having reduced odor comprising (I) reacting a mixture comprising an alkenyl functional polyether, a polydiorganosiloxane-polyorganohydrogensiloxane copolymer, and a homogeneous transition metal hydrosilylation catalyst and (II) subjecting the product of (I) to hydrogen gas.

This invention also relates to a method of making a silicone polyether copolymer having reduced odor comprising (I) subjecting to hydrogen gas a mixture comprising (A) a silicone polyether copolymer, (B) 0.01 to 100 parts by weight of a homogeneous transition metal hydrosilylation catalyst for every one million parts by weight of (A), and (C) 1 to 99 parts by weight per 100 parts by weight of (A) of a mixture of impurities comprising unreacted unsaturated polyethers.

It is an object of this invention to reduce the amount of olefinic species present in the final silicone polyether product mixture which are precursors to odorous compounds.

It is an object of this invention to reduce the amount of odor in the silicone polyether product mixture. These odors are objectionable, particularly in personal care applications.

DETAILED DESCRIPTION OF THE INVENTION

In a first embodiment, this invention relates to a method of making a silicone polyether having reduced odor comprising (I) reacting a mixture comprising: (A) an alkenyl functional polyether compound, (B) a polydiorganosiloxane-polyorganohydrogensiloxane copolymer, and (C) a homogeneous transition metal hydrosilylation catalyst, and (II) subjecting the product of (I) to hydrogen gas.

"Reacting" for the purposes of this invention denotes simply mixing components (A)–(C) and any optional ingredients or heating a mixture of components (A)–(C) and any optional ingredients at temperatures at or above room temperature, preferably at temperatures above 50° C., and more preferably at temperatures from 50–150° C. Preferably a mixture of components (A)–(C) and any optional ingredients is heated at temperatures from 50–150° C.

Component (A), the alkenyl functional polyether compound is preferably a compound having its formula selected from the group consisting of
$CH_2\!=\!CHR(OC_2H_4)_aOR^1$,
$CH_2\!=\!CHR(OC_3H_6)_bOR^1$, $CH_2=CHR(OC_4H_8)_cOR^1$,
$CH_2=CHR(OC_2H_4)_a(OC_3H_6)_b(OC_4H_8)_cOR^1$,
$CH_2=CHR(OC_2H_4)_a(OC_3H_6)_bOR^1$,
$CH_2=CHR(OC_2H_4)_a(OC_4H_8)_cOR^1$, and
$CH_2=CHR(OC_3H_6)_b(OC_4H_8)_cOR^1$
wherein R is selected from the group consisting of an alkylene groups, oxyalkylene groups, arylene groups, oxyarylene groups, aralkylene groups, and oxyaralkylene groups, $R^1$ is selected from the group consisting of a hydrogen atom, an alkyl group, an aryl group, and an acyl group, and a, b, and c independently have an average value from 0.01 to 150.

Alkylene groups are exemplified by methylene, ethylene, butylene, 2-methyltrimethylene, hexamethylene, 3-ethylhexamethylene, octamethylene, decamethylene, dodecamethylene, and octadecamethylene. Oxyalkylene groups are exemplified by oxyethylene, oxybutylene, oxy-2-methyl-trimethylene, oxyhexamethylene, and oxyoctamethylene. Arylene groups are exemplified by phenylene. Oxyarylene groups are exemplified by oxyphenylene. Aralkylene groups are exemplified by phenylenemethylene. Preferably R is methylene.

The group $R^1$ can be a hydrogen atom, an alkyl group, an aryl group, an aralkyl group, or an acyl group. The alkyl groups are exemplified by methyl, ethyl, propyl, butyl, hexyl, octyl, and decyl. The aryl groups are exemplified by phenyl, tolyl, and xylyl. The aralkyl groups are exemplified by benzyl, 2-phenylethyl, and 3-phenylbutyl. The acyl group can have from 1 to 20 carbon atoms and include groups such as acetyl, propionyl, butyryl, isobutyryl, lauroyl, and myristoyl. Preferably the acyl group is a group having the formula $—(O=C)R^4$ wherein $R^4$ denotes a monovalent hydrocarbon group. The monovalent hydrocarbon groups of $R^4$ are exemplified by alkyl groups such as methyl, ethyl, propyl, butyl, hexyl, octyl, and decyl, cycloaliphatic groups such as cyclohexyl, aryl groups such as phenyl, tolyl, and xylyl, and aralkyl groups such as benzyl and 2-phenylethyl. It is preferred that $R^4$ is an alkyl group such as methyl, ethyl, or butyl.

In the above formula, preferably a, b, and c independently have an average value from 0.01 to 1500, especially from 0.01 to 100.

Preferably component (A) is selected from the group consisting of
$CH_2=CHCH_2(OC_2H_4)_aOH$,
$CH_2=CHCH_2(OC_2H_4)_a(OC_3H_6)_bOH$,
$CH_2=CHCH_2(OC_2H_4)_aOCH_3$,
$CH_2=CHCH_2(OC_2H_4)_a(OC_3H_6)_bOCH_3$,
$CH_2=CHCH_2(OC_2H_4)_aO(O=C)CH_3$, and
$CH_2=CHCH_2(OC_2H_4)_a(OC_3H_6)_bO(O=C)CH_3$
wherein a has an average value of 0.01 to 100, and b has an average value of 0.01 to 100.

Component (A) in this invention, is generally present at levels of 1 to 99 weight percent, and preferably from 20 to 85 weight percent of the total composition.

Component (B) in the method of this invention is an a diorganosiloxane-organohydrogensiloxane copolymer. The organo substituent is exemplified by monovalent hydrocarbon groups having from 1 to 20 carbon atoms exemplified by alkyl groups such as methyl, ethyl, propyl, butyl, hexyl, octyl, and decyl, cycloaliphatic groups such as cyclohexyl, aryl groups such as phenyl, tolyl, and xylyl, and aralkyl groups such as benzyl and 2-phenylethyl. It is highly preferred that the organo substituents are methyl. The monovalent hydrocarbon group can also be any monovalent hydrocarbon group noted above which has at least one of its hydrogen atoms replaced with a halogen, such as fluorine, chlorine, or bromine, and these monovalent hydrocarbon groups, are exemplified by $CF_3CH_2CH_2—$ and $C_4F_9CH_2CH_2—$. Each organo substituent can be the same or different, as desired.

Component (B) is exemplified by dimethylhydrogensiloxy-terminated polydimethylsiloxane-polymethylhydrogensiloxane copolymers and trimethylsiloxyterminated polydimethylsiloxane-polymethylhydrogensiloxane copolymers. Preferably component (B) is a trimethylsiloxy-terminated polydimethylsiloxane-polymethylhydrogensiloxane copolymer.

The viscosity at 25° C. of Component (B) is generally from 0.65 to 4000 mm²/s, and is preferably from 0.8 to 2500 mm²/s (1 mm²/s=1 centistoke).

The diorganosiloxane-organohydrogensiloxane copolymers of Component (B) are well known in the art, many of these being available commercially, and further description thereof is considered unnecessary.

Component (B) in this invention, is generally present at levels of 1 to 99 weight percent, and preferably from 15 to 80 weight percent of the total composition.

Component (C) in the method of this invention is a homogeneous transition metal hydrosilylation catalyst. From the standpoint of simplicity and economy it is highly desirable that hydrosilylation and hydrogenation are achieved with the same catalyst and by a single charge of catalyst but that is not necessary for the successful operation of this invention. Different homogeneous transition metal hydrosilylation catalysts could be used for the hydrosilylation and hydrogenation steps.

For purposes of this invention, homogeneous denotes a material that is soluble in the hydrosilylation-hydrogenation reaction matrix as a whole or in one or more of the individual components of the reaction matrix. For example, a liquid catalyst or a solid catalyst dissolved in a liquid carrier that forms small dispersible droplets, in the form of an emulsion or microemulsion, is a homogeneous catalyst and thus would be suitable for use as component (C) in this invention.

Specific examples of homogeneous transition metal hydrosilylation catalysts which are suitable for use as component (C) include transition metal complexes, transition metal acids, or transition metal salts. Transition metal complexes are exemplified by transition metal complexes obtained by a method comprising reacting a transition metal acid such as chloroplatinic acid with an olefin such as an aliphatically unsaturated organosilicon compound exemplified by divinyltetramethyldisiloxane. Another transition metal complex suitable for use in the method of this invention is obtained by a method comprising reacting a transition metal acid such as chloroplatinic acid with an alcohol.

Transition metal acids are exemplified by chloroplatinic acid, bromoplatinic acid, chloroiridic acid, and chloroosmic acid. Transition metal salts are exemplified by potassium hexachloroplatinate, potassium hexaiodoplatinate, sodium hexachloroplatinate hexahydrate, potassium tetrabromoplatinate, potassium tetrachloroplatinate, and sodium tetrachloroplatinate.

It is generally accepted within the art that when compounds such as those above are added as catalysts they undergo transformation during the ensuing chemistry to form other species which are the true catalysts. The exact identity of such reacting species is controversial and depends on the chemical system involved, the level of impurities and other factors. Thus of particular importance and covered by this invention are any alcohol and/or olefinic modifications of transition metal compounds such as those delineated above, such modifications commonly referred to as transition metal complexes, regardless of whether the alcohol and/or olefinic modifications are introduced as such or generated by the reacting system. All complexes of transition metals are deemed as included under the definition "transition metal complexes". Of significant importance and specifically included are transition metal complexes produced from silicon-substituted olefins and transition metal acids.

Particularly preferred as component (C) in the method of this invention is a form of chloroplatinic acid, either as the commonly available hexahydrate form or as the anhydrous form, as taught by Speier, U.S. Pat. No. 2,823,218, incorporated herein by reference. Another particularly useful catalyst is the composition that is obtained by a method comprising reacting chloroplatinic acid with an aliphatically unsaturated organosilicon compound such as divinyltetramethyldisiloxane, as disclosed by Willing, U.S. Pat. No. 3,419,593, incorporated herein by reference, because of its easy dispersibility in organosilicon systems.

The amount of homogeneous transition metal hydrosilylation catalyst that is used is not narrowly limited as long as there is a sufficient amount to accelerate a reaction between the dimethylsiloxane-organohydrogensiloxane copolymer and alkenyl functional polyether compound. The exact necessary amount of this catalyst component will depend on the particular catalyst utilized and is not easily predictable. Preferably catalyst (C) is added in an amount such that it provides 0.01 to 100 parts of transition metal for every one million parts of (A), and preferably 1.0 to 20.0 parts by weight of transition metal for every one million parts by weight of (A). The mixture of Step (I) in the method of this invention can further comprise an organic solvent exemplified by alcohols such as ethanol or isopropanol, aromatic hydrocarbons such as toluene or xylene, ethers such as dioxane and tetrahydrofuran (THF), aliphatic hydrocarbons, esters, ketones, and chlorinated hydrocarbons.

The organic solvent is generally present at levels of 5 to 50 weight parts, and preferably from 15 to 30 weight parts per 100 parts of (A)+(B)+(C).

Step (II) in the method of this invention is subjecting the product of (I) to hydrogen gas. Generally the product of Step (I) is exposed to hydrogen gas in a container, and preferably the container is pressurized with molecular hydrogen to a pressure of from 1 to 10,000 psi, and especially from 10 to 200 psi. Typically the product of (I) is subjected to the action of hydrogen at temperatures of from about 20 to 200° C. and at a pressure of from about 10 to 200 psi for a period of about 0.1 to 48 hours. Preferably the hydrogen is allowed to act on the product of Step (I) at temperatures of from 20 to 150° C. and a pressure of from 10 to 200 psi.

Materials known in the art to stabilize systems to undesired ambient processes such as oxidation may optionally be added to hydrogenated product mixture of Step (II). These materials are exemplified by tocopherols (e.g. Vitamin E), and hydroquinones. These stabilizing agents act to keep the quality of the hydrogenated product mixture consistent over time.

In a second embodiment, this invention relates to a method of making a silicone polyether copolymer having reduced odor comprising (I) subjecting to hydrogen gas a mixture comprising (A) a silicone polyether copolymer having the formula $R^1R^2SiO(R^2SiO)_a(RXSiO)_bSiR^2R^1$ wherein R is a monovalent hydrocarbon group having from 1 to 20 carbon atoms, X is a polyoxyalkylene group selected from the group consisting of —$R^2(OC_2H_4)_cOR^3$, —$R^2(OC_2H_4)_c(OC_3H_6)_dOR^3$, —$R^2(OC_2H_4)_c(OC_4H_8)_eOR^3$, —$R^2(OC_3H_6)_d(OC_4H_8)_eOR^3$, and —$R^2(OC_2H_4)_c(OC_3H_6)_d(OC_4H_8)_eOR^3$, wherein $R^1$ is R or X, $R^2$ is a divalent hydrocarbon group having from 2 to 20 carbon atoms, $R^3$ is selected from a hydrogen atom, an alkyl group, an aryl group, an aralkyl group, or an acyl group, a has an average value from 1 to 2000, b has an average value from 1 to 500, and c, d, and e independently have an average value from 0.01 to 150, (B) a homogeneous transition metal hydrosilylation catalyst in an amount sufficient to provide 0.01 to 100 parts by weight of transition metal for every one million parts by weight of (A), and (C) 1 to 99 parts by weight per 100 parts by weight of (A) of a mixture of impurities comprising unreacted unsaturated polyethers.

In the above formula for Component (A), R is a monovalent hydrocarbon group having from 1 to 20 carbon atoms exemplified by alkyl groups such as methyl, ethyl, propyl, butyl, hexyl, octyl, and decyl, cycloaliphatic groups such as cyclohexyl, aryl groups such as phenyl, tolyl, and xylyl, and aralkyl groups such as benzyl and phenylethyl. It is preferred that R is selected from methyl or phenyl. The several R radicals can be identical or different, as desired.

The group $R^2$ is a divalent hydrocarbon group having from 2 to 20 carbon atoms which is exemplified by alkylene groups exemplified by ethylene, propylene, butylene, pentylene, trimethylene, 2-methyltrimethylene, pentamethylene, hexamethylene, 3-ethylhexamethylene, octamethylene, —$CH_2(CH_3)CH$—, —$CH_2CH(CH_3)CH_2$—, —$(CH_2)_{18}$—, and cycloalkylene radicals such as cyclohexylene, arylene radicals such as phenylene, combinations of divalent hydrocarbon radicals such as benzylene (—$C_6H_4CH_2$—), and oxygen containing groups such as —$CH_2OCH_2$—, —$CH_2CH_2CH_2OCH_2$—, —$CH_2CH_2OCH_2CH_2$—, —$(C=O)OCH_2CH_2O(O=C)$—, —$CH_2CH_2OCH(CH_3)CH_2$—, and —$CH_2OCH_2CH_2OCH_2CH_2$—. Preferred alkylene groups have from 2 to 8 carbon atoms.

The group $R^3$ can be a hydrogen atom, an alkyl group, an aryl group, an aralkyl group, or an acyl group. The alkyl groups are exemplified by methyl, ethyl, propyl, butyl, hexyl, octyl, and decyl. The aryl groups are exemplified by phenyl, tolyl, and xylyl. The aralkyl groups are exemplified by benzyl, 2-phenylethyl, and 3-phenylbutyl. The acyl group can have from 1 to 20 carbon atoms and include groups such as acetyl, propionyl, butyryl, isobutyryl, lauroyl, and myristoyl. Preferably the acyl group is a group having the formula —$(O=C)R^4$ wherein $R^4$ denotes a monovalent hydrocarbon group. The monovalent hydrocarbon groups of $R^4$ are as delineated above for R. It is preferred that $R^4$ is a lower alkyl group such as methyl, ethyl, or butyl.

In the above formula for Component (A), preferably a has an average value from 20 to 500, b has an average value from 1 to 500, and c, d, and e independently have an average value from 0.01 to 100. It is especially preferred that a has an average value from 100 to 300, b has an average value from 1 to 50, and c, d, and e independently have an average value from 0.01 to 100.

Preferably Component (A) is a silicone polyether copolymer having the formula $Me_3SiO(Me_2SiO)_a(MeXSiO)_bSiMe_3$, wherein X is selected from the group consisting of —$(CH_2)_n(OC_2H_4)_cOH$, —$(CH_2)_n(OC_2H_4)_c(OC_3H_6)_dOH$, —$(CH_2)_n(OC_2H_4)_cOCH_3$, —$(CH_2)_n(OC_2H_4)_c(OC_3H_6)_dOCH_3$, —$(CH_2)_n(OC_2H_4)_cO(O=C)CH_3$, and —$(CH_2)_n(OC_2H_4)_c(OC_3H_6)_dO(O=C)CH_3$ wherein Me denotes methyl, a has an average value from 100 to 300, b has an average value from 1 to 50, n has a value of 2 to 10, c has an average value of 0.01 to 100, and d has an average value of 0.01 to 100.

Component (B), the homogeneous transition metal hydrosilylation catalyst, is as described above, including preferred embodiments thereof. Preferably component (B) is present in an amount sufficient to provide 2 to 20 parts by weight of transition metal for every one million parts by weight of (A).

Component (C) the unsaturated unreacted polyethers are exemplified by allyl polyethers, propenyl polyethers, vinyl polyethers, and mixtures thereof.

The mixture of (A), (B), and (C) is subjected to hydrogen gas as described hereinabove in the first embodiment of this invention including preferred embodiments thereof.

As described above in the first embodiment of this invention, materials known in the art to stabilize systems to undesired ambient processes such as oxidation may optionally be added to hydrogenated product mixture of Step (I). These materials are exemplified by tocopherols (e.g. Vitamin E), and hydroquinones. These stabilizing agents act to keep the quality of the hydrogenated product mixture consistent over time.

The method of this invention reduces the amount of olefinic species present which are precursors to odorous compounds. Thus the method of this invention reduces the amount of odor in the silicone polyether copolymer product. These odors are objectionable, particularly in personal care applications.

The silicone polyethers of this invention are particularly useful in hair care formulations, skin care formulations, antiperspirant and deodorant formulations, cosmetics, topical pharmaceuticals, pressure sensitive adhesives used in transdermal drug delivery, in preparing silicone emulsions, as components of inks, and paints, and as additives to plastics.

EXAMPLES

The silicone polyethers of this invention were tested by a Sensory Panel for Odor in the following manner: The candidate silicone polyether was formulated as follows: 4.0 wt. % silicone polyether, 48.0 wt. % decamethylcyclopentasiloxane, 48.0 wt. % water (pH 5). The silicone polyether, decamethylcyclopentasiloxane, and water were mixed with a Lightin® mixer for 3 minutes at 1000 rpm followed by 3 minutes at 1500 rpm. The resulting mixture was stored at 50° C. for 3 months. An olfactory panel determined the level of odor and designated the level with a numerical rating of 1 to 4 where 1 indicated the least odor and 4 indicated the most odor.

Silicone-polyether copolymers are generally prepared by the platinum-catalyzed addition of siloxane hydrides to olefinic polyethers. The uptake of molecular hydrogen without added hydrogenation catalyst demonstrates the hydrogenating activity of the platinum catalyst left over from the hydrosilylation coupling reaction.

Example 1

A silicone-polyether copolymer was prepared by heating a mixture of 129 g (0.224 equiv. of C=C) of an alkenyl functional polyether having the average formula $CH_2=CHCH_2(OC_2H_4)_7OH$, 50.8 g of trimethylsiloxy-terminated polydimethylsiloxane-polymethylhydrogensiloxane copolymer having a viscosity at 25° C. of about 7.2 mm²/s, (0.182 equiv. of SiH), 20.2 g of 2-propanol and 0.2 cc of a 1 wt. % solution of chloroplatinic acid, until the level of SiH was reduced to a low level (2 ppm as shown by FTIR). While still warm the crude silicone polyether copolymer was transferred to a Parr hydrogenation bottle and with no further additions of hydrogenation catalyst the system was purged three times with hydrogen gas and was pressurized with molecular hydrogen to 50 psi. The bottle was then warmed to 70° C. while agitated. The absorption of hydrogen was monitored by pressure drop. After two hours the pressure stopped falling and the excess hydrogen was vented. The copolymer was transferred to a flask, devolatilized to a final temperature of 90° C. and a pressure of 30 mm of Hg and held for one hour. The silicone polyether had a index of refraction of 1.4530. When this silicone polyether was evaluated for odor according to the procedure described above it was given a rating of 2.

Example 2

A mixture containing a silicone-polyether copolymer having the average formula $Me_3SiO(Me_2SiO)_{396}(MeXSiO)_4SiMe_3$ where X is a group having the formula $-(CH_2)_3(OC_2H_4)_{18}(OC_3H_6)_{18}OH$, containing chloroplatinic acid in an amount such that it provides approximately 3 weight parts of platinum metal for every one million parts of silicone-polyether copolymer, and containing 8 weight parts of unreacted unsaturated polyethers per 100 weight parts of silicone-polyether copolymer, was subjected to an odor-reducing treatment as follows: With no additions of hydrogenation catalyst, 240 g of the silicone polyether was charged to a Parr hydrogenation bottle, purged three times with hydrogen gas and pressurized with 60 psi of molecular hydrogen. The system was then agitated and heated to 70° C. After one hour the hydrogen pressure stopped falling and the excess hydrogen was vented. The copolymer was devolatilized to a final temperature of 105° C. and a pressure of 25 mm of Hg. The silicone polyether had an index of refraction of 1.4181. When this copolymer was evaluated for odor according to procedure described above it was given a rating of 1.

Comparative Example 1

A silicone-polyether copolymer having the average formula $Me_3SiO(Me_2SiO)_{8.7}(MeXSiO)_{3.7}SiMe_3$ where X is a group having the formula $-(CH_2)_3(OC_2H_4)_7OH$ was subjected to an odor reducing treatment as follows: A Parr hydrogenation bottle was charged with 300 g of the silicone polyether, 3.0 g of water, 0.5 g of acetic acid and 0.6 g of 3% palladium on carbon and purged three times with hydrogen gas. Hydrogen pressure of 60 psi was imposed and the system was agitated and warmed to 70° C. Absorption of hydrogen occurred over a period of 5.5 hours. The system was vented and the crude product was filtered through a cake of Perlite. The product was devolatilized on a thin film stripper at 100° C. and a pressure of 10 mm of Hg. When this silicone polyether was evaluated for odor according to the procedure described above it was given a rating of 3.

Comparative Example 2

The procedure of Example 3 was repeated with 1.0 g of Tonsil clay(strong acid) instead of acetic acid. When the isolated copolymer was evaluated for odor according to the procedure described above it was given a rating of 3.

Comparative Example 3

The silicone-polyether described in example 2 but without any odor-reducing treatment was evaluated for odor according the procedure described above and it was given a rating of 4.

That which is claimed is:

1. A method of making a silicone polyether having reduced odor comprising:
   (I) reacting a mixture comprising:
      (A) an alkenyl functional polyether compound;
      (B) a polydiorganosiloxane-polyorganohydrogensiloxane copolymer; and
      (C) a homogeneous transition metal hydrosilylation catalyst; and
   (II) subjecting the product of (I) to hydrogen gas.

2. A method according to claim 1, wherein (A) is a compound having its formula selected from the group consisting of $CH_2=CHR(OC_2H_4)_aOR^1$,
$CH_2=CHR(OC_3H_6)_bOR^1$,
$CH_2=CHR(OC_4H_8)_cOR^1$,
$CH_2=CHR(OC_2H_4)_a(OC_3H_6)_b(OC_4H_8)_cOR^1$,
$CH_2=CHR(OC_2H_4)_a(OC_3H_6)_bOR^1$,
$CH_2=CHR(OC_2H_4)_a(OC_4H_8)_cOR^1$, and
$CH_2=CHR(OC_3H_6)_b(OC_4H_8)_cOR^1$ wherein R is selected from the group consisting of an alkylene groups, oxyalkylene groups, arylene groups, oxyarylene groups, aralkylene groups, and oxyaralkylene groups, $R^1$ is selected from the group consisting of a hydrogen atom, an alkyl group, an aryl group, and an acyl group, and a, b, and c independently have an average value from 0.01 to 150.

3. A method according to claim 2, wherein R is methylene, and R1 is selected from the group consisting of a hydrogen atom, methyl, and —(O=C)CH$_3$.

4. A method according to claim 2, wherein (A) is selected from the group consisting of $CH_2=CHCH_2(OC_2H_4)_aOH$,
$CH_2=CHCH_2(OC_2H_4)_a(OC_3H_6)_bOH$,
$CH_2=CHCH_2(OC_2H_4)_aOCH_3$,
$CH_2=CHCH_2(OC_2H_4)_a(OC_3H_6)_bOCH_3$,
$CH_2=CHCH_2(OC_2H_4)_aO(O=C)CH_3$, and
$CH_2=CHCH_2(OC_2H_4)_a(OC_3H_6)_bO(O=C)CH_3$ wherein a has an average value of 0.01 to 100, and b has an average value of 0.01 to 100.

5. A method according to claim 1, wherein (B) is a dimethylhydrogensiloxy-terminated polydimethylsiloxane-polymethylhydrogensiloxane copolymer or a trimethylsiloxy-terminated polydimethylsiloxane-polymethylhydrogensiloxane copolymer.

6. A method according to claim 1, wherein (B) is a trimethylsiloxy-terminated polydimethylsiloxane-polymethylhydrogensiloxane copolymer having a viscosity at 25° C. of from 0.8 to 2500 mm²/s.

7. A method according to claim 4, wherein (B) is a trimethylsiloxy-terminated polydimethylsiloxane-polymethylhydrogensiloxane copolymer having a viscosity at 25° C. of from 0.8 to 2500 mm²/s.

8. A method according to claim 1, wherein (C) is a transition metal complex, transition metal acid, or transition metal salt.

9. A method according to claim 8, wherein the transition metal complex is obtained by a method comprising reacting a transition metal acid with an olefin or an alcohol.

10. A method according to claim 8, wherein the transition metal acid is chloroplatinic acid, bromoplatinic acid, chloroiridic acid, or chloroosmic acid.

11. A method according to claim 8, wherein the transition metal salt is potassium hexachloroplatinate, potassium hexaiodoplatinate, sodium hexachloroplatinate hexahydrate, potassium tetrabromoplatinate, potassium tetrachloroplatinate, or sodium tetrachloroplatinate.

12. A method according to claim 9, wherein the transition metal acid is chloroplatinic acid and the olefin is an aliphatically unsaturated organosilicon compound.

13. A method according to claim 12, wherein the aliphatically unsaturated organosilicon compound is divinyltetramethyldisiloxane.

14. A method according to claim 7, wherein (C) is chloroplatinic acid or a transition metal complex obtained by a method comprising reacting chloroplatinic acid with divinyltetramethyldisiloxane.

15. A method according to claim 1, wherein the mixture of Step (I) further comprises an organic solvent.

16. A method according to claim 1, wherein Step (II) comprises subjecting the product of (I) to hydrogen gas at temperatures of from 20 to 200° C. and at a pressure of from 10 to 200 psi for a period of about 0.1 to 48 hours.

17. A method according to claim 14, wherein Step (II) comprises subjecting the product of (I) to hydrogen gas at temperatures of from 20 to 200° C. and at a pressure of from 10 to 200 psi for a period of about 0.1 to 48 hours.

18. A method according to claim 1, wherein the method further comprises adding an ingredient selected from the group consisting of tocopherols and hydroquinones to the product of Step (II).

19. A method of making a silicone polyether copolymer having reduced odor comprising:
   (I) subjecting to hydrogen gas a mixture comprising:
      (A) a silicone polyether copolymer having the formula $R^1R_2SiO(R_2SiO)_a(RXSiO)_bSiR_2R^1$ wherein R is a monovalent hydrocarbon group having from 1 to 20 carbon atoms,
X is a polyoxyalkylene group selected from the group consisting of
—$R^2(OC_2H_4)_cOR^3$, —$R^2(OC_2H_4)_c(OC_3H_6)_dOR^3$, —$R^2(OC_2H_4)_c(OC_4H_8)_eOR^3$, —$R^2(OC_3H_6)_d(OC_4H_8)_eOR^3$, and —$R^2(OC_2H_4)_c(OC_3H_6)_d(OC_4H_8)_eOR^3$,
wherein $R^1$ is R or X, $R^2$ is a divalent hydrocarbon group having from 1 to 20 carbon atoms, $R^3$ is selected from a hydrogen atom, an alkyl group, an aryl group, an aralkyl group, or an acyl group, a has an average value from 1 to 2000, b has an average value from 1 to 500, and c, d, and e independently have an average value from 0.01 to 150;
      (B) a homogeneous transition metal hydrosilylation catalyst present in an amount sufficient to provide 0.01 to 100 parts by weight of transition metal for every one million parts by weight of (A); and
      (C) 1 to 99 parts by weight per 100 parts by weight of (A) of a mixture of impurities comprising unreacted unsaturated polyethers.

20. A method according to claim 19, wherein (A) is a silicone polyether copolymer having the formula $Me_3SiO(Me_2SiO)_a(MeXSiO)_bSiMe_3$, wherein X is selected from the group consisting of
—$(CH_2)_n(OC_2H_4)_cOH$, —$(CH_2)_n(OC_2H_4)_c(OC_3H_6)_dOH$, —$(CH_2)_n(OC_2H_4)_cOCH_3$, —$(CH_2)_n(OC_2H_4)_c(OC_3H_6)_d OCH_3$, —$(CH_2)_n(OC_2H_4)_cO(O=C)CH_3$, and —$(CH_2)_n(OC_2H_4)_c(OC_3H_6)_dO(O=C)CH_3$ wherein Me denotes methyl, a has an average value from 100 to 300, b has an average value from 1 to 50, n has a value of 2 to 10, c has an average value of 0.01 to 100, and d has an average value of 0.01 to 100.

21. A method according to claim 19, wherein (B) is chloroplatinic acid or a transition metal complex obtained by a method comprising reacting chloroplatinic acid with divinyltetramethyldisiloxane.

22. A method according to claim 20, wherein (B) is chloroplatinic acid or a transition metal complex obtained by a method comprising reacting chloroplatinic acid with divinyltetramethyldisiloxane.

23. A method according to claim 19, wherein the unreacted unsaturated polyethers are allyl polyethers, propenyl polyethers, vinyl polyethers, or mixtures thereof.

24. A method according to claim 19, wherein Step (I) comprises subjecting the mixture of (I) to hydrogen gas at temperatures of from 20 to 200° C. and at a pressure of from 10 to 200 psi for a period of about 0.1 to 48 hours.

25. A method according to claim 22, wherein Step (I) comprises subjecting the mixture of (I) to hydrogen gas at temperatures of from 20 to 200° C. and at a pressure of from 10 to 200 psi for a period of about 0.1 to 48 hours.

26. A product produced in accordance with the method of claim 1.

27. A product produced in accordance with the method of claim 19.

* * * * *